United States Patent [19]
Lee et al.

[11] Patent Number: 5,891,196
[45] Date of Patent: *Apr. 6, 1999

[54] METHOD FOR ACTIVELY BINDING HEPARIN TO CROSSLINKED BIOLOGICAL TISSUES

[75] Inventors: Catherine Ting Lee, Laguna Hills; Jun Yang, Dove Canyon, both of Calif.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 843,504

[22] Filed: Apr. 16, 1997

[51] Int. Cl.$^6$ ..................................................... A61L 17/00
[52] U.S. Cl. .................................. 8/94.11; 623/1; 623/2; 623/15; 623/11; 623/13; 525/54.2; 514/56; 514/822; 523/112; 427/2.24; 427/2.1; 427/2.25
[58] Field of Search ................................. 8/94.11; 623/1, 623/2, 15, 11, 13; 525/54.2; 514/56, 822; 523/112; 427/2.24, 2.1, 2.25

[56] References Cited

U.S. PATENT DOCUMENTS

| | | |
|---|---|---|
| 3,673,612 | 7/1972 | Merrill et al. . |
| 3,810,781 | 5/1974 | Eriksson et al. . |
| 4,118,485 | 10/1978 | Eriksson et al. . |
| 4,120,649 | 10/1978 | Schechter . |
| 4,250,041 | 2/1981 | Babson et al. . |

(List continued on next page.)

FOREIGN PATENT DOCUMENTS

| | | |
|---|---|---|
| 0 103 947 A2 | 3/1984 | European Pat. Off. . |
| 0 357 242 A1 | 3/1990 | European Pat. Off. . |
| 0 404 683 A2 | 12/1990 | European Pat. Off. . |
| 0 423 369 A1 | 4/1991 | European Pat. Off. . |
| 2 309 245 | 12/1976 | France . |
| 26 10 698 | 9/1976 | Germany . |
| 27 48 858 | 10/1977 | Germany . |
| 2 001 663 | 2/1979 | United Kingdom . |
| 1 583 008 | 1/1981 | United Kingdom . |
| WO 84/01879 | 5/1984 | WIPO . |
| WO 91/169332 | 11/1991 | WIPO . |
| WO 93/14127 | 7/1993 | WIPO . |

OTHER PUBLICATIONS

Miyata et al, "A new method to give an antithirombogenicity to biological materials and its successful application to vascular grafts," Trans. Am. Artif. Intern. Organs, vol. XXIX, (month unknown), pp. 363–368, 1983.

(List continued on next page.)

Primary Examiner—Alan Diamond
Attorney, Agent, or Firm—Robert D. Buyan; Guy L. Cumberbatch

[57] ABSTRACT

Methods for binding heparin to biological or synthetic materials which are to be implanted within a mammalian body. In instances where connective tissue proteins or other components of the material having adequate carboxyl groups present thereon, the method comprises a) contacting the material with a carboxyl-activating agent, b) contacting the material with a polyamine compound to form amide-bound polyarnine side chains at the sites of the previously activated carboxyl groups, and c) contacting the material with heparin such that heparin will become bound to the amino groups on the polyamine side chains. In other applications wherein the connective tissue proteins or other molecular entities of the material are devoid of or deficient in carboxyl groups, the method will comprise a) contacting the material with a carboxyl-activating agent in combination with a polyamine compound which has functional carboxyl groups thereon such that at least some of the functional carboxyl groups of the polyamine compound will become activated and will react with some of the amino groups on the polyamine compounds to form a polyamine network interlocked within the molecular structure of the material, and b) contacting the material with heparin such that heparin will become bound to amino groups on the polyamine network.

34 Claims, 7 Drawing Sheets

U.S. PATENT DOCUMENTS

| | | |
|---|---|---|
| 4,331,697 | 5/1982 | Kudo et al. . |
| 4,378,224 | 3/1983 | Nimni et al. . |
| 4,502,159 | 3/1985 | Woodroff et al. . |
| 4,565,740 | 1/1986 | Gölander et al. . |
| 4,613,517 | 9/1986 | Williams et al. . |
| 4,648,881 | 3/1987 | Carpentier et al. . |
| 4,690,973 | 9/1987 | Noishiki et al. . |
| 4,704,131 | 11/1987 | Noishiki et al. . |
| 4,806,595 | 2/1989 | Noishiki et al. ........................ 525/54.2 |
| 4,820,302 | 4/1989 | Woodroof . |
| 4,828,561 | 5/1989 | Woodroof . |
| 4,885,005 | 12/1989 | Nashef et al. . |
| 4,976,733 | 12/1990 | Girardot . |
| 5,002,256 | 3/1991 | Bedford . |
| 5,043,278 | 8/1991 | Nagaoka et al. . |
| 5,049,403 | 9/1991 | Larm et al. . |
| 5,132,108 | 7/1992 | Narayanan et al . |
| 5,134,192 | 7/1992 | Feijen et al. . |
| 5,159,050 | 10/1992 | Onwumere . |
| 5,215,886 | 6/1993 | Patel et al. . |
| 5,217,743 | 6/1993 | Farah . |
| 5,229,172 | 7/1993 | Cahalan et al. . |
| 5,270,046 | 12/1993 | Sakamotol et al. . |
| 5,308,641 | 5/1994 | Cahalan et al. . |
| 5,336,518 | 8/1994 | Narayanan et al. . |
| 5,338,770 | 8/1994 | Winters et al. . |
| 5,342,693 | 8/1994 | Winters et al. . |
| 5,350,800 | 9/1994 | Verhoeven et al. . |
| 5,356,433 | 10/1994 | Rowland et al. . |
| 5,403,827 | 4/1995 | De-Ambrosi . |
| 5,415,938 | 5/1995 | Cahalan et al. . |

OTHER PUBLICATIONS

Noishiki, et al., "Application of Porous Heparinized Polymer to Vascular Graft", Trans ASAIO 27:213–218, 1981 (Month Unknown).

Miyata, et al., "A New Method to Give an Antithrombogenicity to Biological Materials and Its Sucessful Application to Vascular Grafts", Trans ASAIO 29:363–368, 1983, (Month Unknown).

Noishiki, et al., "Antiadhesive Collagen Membrane with Heparin Slow Release", The 11th Annual Meeting of the Society for Biomaterials, p. 99, San Diego, Apr. 25–28, 1985.

Noishiki, et al., "Successful Animal Study of Small Caliber Heparin–Protamine–Collagen Vascular Grafts", Trans ASAIO 31:102–106, 1985 (Month Unknown).

Noishiki, et al., A Simple Method to Heparinize Biological Materials J Biomed Mater Res, 20:337–346, 1986, (Month Unknown).

Noishiki, et al., "Antiadhesive Collagen Membrane with Heparin Slow Release", J Bioactive Bicompatible Polymers, 2:325–333, 1987, (Month Unknown).

Satoh, et al., "Development of an Autologous Connective Tissue Tube as a Small Caliber Vascular Substitute", Trans ASAIO, 34: 655–660, 1988, (Month Unknown).

Miyata, et al., "Biodegradable Antiadhesive Collagen Membrane with Heparin Slow Release", The 3rd World Biomaterials Congress, p. 528, Apr. 21–25, Tokyo 1988.

METHOD FOR ACTIVELY BINDING HEPARIN TO CROSSLINKED BIOLOGICAL TISSUES

FIELD OF THE INVENTION

The present invention relates generally to methods for manufacturing devices, and more particularly to methods for manufacturing surgically implantable bioprostheses having improved biocompatability.

BACKGROUND OF THE INVENTION i. Biological Tissue Grafts and Prostheses

Collagen, and to a lesser extent elastin, are the major connective tissue proteins which make-up the connective tissue framework of most biological tissues. The relative pliability or rigidity of each biological tissue is largely determined by the relative amounts of collagen and elastin present in the tissue and/or by the physical configuration and conformation (e.g., structural lattice) formed by the connective tissue proteins.

The prior art has included numerous surgically-implantable bioprosthetic grafts and prostheses (referred to herebelow collectively as "bioprostheses") which are formed wholly or partially of chemically fixed (i.e., tanned) biological tissue. The chemical fixation of these biological tissues is typically accomplished by contacting the tissue with one or more chemicals which will crosslink collagen and elastin molecules which are present within the tissue. Such crosslinking of the collagen and elastin serves to preserve the tissue so that the tissue may be used as, or incorporated into, bioprosthetic devices intended for long term implantation or attachment to a patient's body. Examples of biological materials which have heretofore been utilized as bioprostheses include cardiac valves, blood vessels, skin, dura mater, pericardium, ligaments and tendons. These anatomical structures typically contain connective tissue matrices, formed of collagen and elastin, and the cellular parenchyma of each tissue is disposed within and supported by its connective tissue matrix.

Each collagen molecule consists of three (3) polypeptide chains which are intertwined in a coiled helical conformation. Chemical fixatives (i.e., tanning agents) used to preserve biological tissues form chemical crosslinkages between functional groups on the polypeptide chains within a given collagen molecules, or between functional groups on adjacent collagen molecules.

When chemical crosslinkages are formed between polypeptide chains within a single collagen or elastin molecule, such crosslinkages are termed "intramolecular", while crosslinkages formed between polypeptide chains of different collagen or elastin molecules are termed "intermolecular".

Elastin fibers are built by crosslinking (natural linkage) of repeating units of smaller molecules in essentially fibrous strands maintained by rigid crosslinking involving desmosine and isodesmosine. Those chemical fixatives which are used to form crosslinkages between the amino groups of collagen molecules also tend to form such crosslinkages between amino groups of elastin molecules. However, the amount of elastin present in most biological tissues is substantially less than the amount of collagen present therein.

Chemical fixative agents which have previously been utilized to crosslink collagen and/or elastin in biological tissues include; formaldehyde, glutaraldehyde, dialdehyde starch, hexamethylene diisocyanate and certain polyepoxy compounds.

Glutaraldehyde is the most widely used agent for fixing biological tissues to be as bioprostheses and there are currently a number of commercially available glutaraldehyde-fixed bioprosthetic devices, such as, heart valves of porcine origin having support frames or stents (Carpentier-Edwards® Stented Porcine Bioprosthesis; Baxter Healthcare Corporation; Edwards CVS Division, Irvine, Calif. 92714-5686), prosthetic heart valves formed of a metal frame having leaflets formed of bovine pericardial tissue mounted on the frame (e.g., Carpentier-Edwards® Pericardial Bioprosthesis, Baxter Healthcare Corporation, Edwards CVS Division; Irvine, Calif. 92714-5686) and stentless porcine aortic prostheses (e.g., Edwards® PRIMA™ Stentless Aortic Bioprosthesis, Baxter Edwards AG, Spierstrasse 5, GH6048, Horn, Switzerland).

ii. Calcification of Biological Tissue Grafts & Prostheses

One problem associated with the implantation of bioprosthetic grafts is that they tend to undergo in situ calcification following implantation. Such calcification can result in undesirable stiffening, degradation and premature failure of the bioprosthesis. Both intrinsic and extrinsic calcification have been known to occur, although the exact mechanism(s) by which such calcification occurs is unknown.

The factors which determine the rate at which chemically-fixed bioprosthetic grafts undergo calcification have not been fully elucidated. However, factors which are thought to influence the rate of calcification include:

a) patient's age;

b) existing metabolic disorders (i.e., hypercalcemia, diabetes, etc.);

c) dietary factors;

d) race;

e) infection;

f) parenteral calcium administration;

g) dehydration;

h) distortion/mechanical factors;

i) inadequate anti-coagulation therapy during initial period following surgical implantation; and j) host tissue responses.

Glutaraldehyde-fixed bioprosthetic grafts have been observed to calcify sooner than grafts which have been fixed by non-aldehyde fixative agents. Thus, non-aldehyde fixatives, such as polyepoxy compounds, may be useful for manufacturing bioprosthetic graft materials which exhibit improved (i.e., lessened) propensity for calcification. Examples of polyepoxy compounds which may be used to crosslink connective tissue proteins include: ethylene, polyethylene glycol diglycidyl ether (Denacol EX-810, Nagase Chemical, Co., Osaka, Japan) and glycerol polyglycidyl ether (Denacol EX-313, Nagase Chemical, Co., Osaka, Japan).

The prior art has also included numerous reports and publications which purport to describe techniques or process which will mitigate in situ calcification of implanted biological tissues. These publications include; U.S. Pat. No. 4,885,005 (Nashef et al.) entitled Surfactant Treatment of Implantable Biological Tissue To Inhibit Calcification; U.S. Pat. No. 4,648,881 (Carpentier et al.) entitled, "Implantable Biological Tissue and Process For Preparation Thereof"; U.S. Pat. No. 4,976,733 (Girardot) entitled, "Prevention of Prosthesis Calcification"; U.S. Pat. No. 4,120,649 (Schechter) entitled, "Transplants"; U.S. Pat. No. 5,002,256 (Carpentier) entitled, "Calcification Mitigation of Bioprosthetic Implants"; EP 103947A2 (Pollock et al.) entitled, "Method For Inhibiting Mineralization of Natural Tissue During Implantation" and WO84/01879 (Nashef et al.) entitled, "Surfactant Treatment of Implantable Biological Tissue to Inhibit Calcification"; and, in Yi, D., Liu, W., Yang, J., Wang, B., Dong, G., and Tan, H.; *Study of Calcification Mechanism and Anticalcification On Cardiac Bioprostheses* Pgs. 17–22, Proceedings of Chinese Tissue Valve Conference, Beijing, China, June 1995.

iii. Biocompatability of Tissue Grafts & Prostheses

The overall biocompatibility (e.g., antigenicity and immunogenicity) of a fixed biological tissue can significantly affect the severity of post-implantation calcification of that tissue, and may also be a factor in the occurrence of other undesirable post-implantation complications or sequelae, such as platelet activation, thrombogenesis, local inflammation, and/or graft failure. The biocompatability (e.g., antigenicity and/or immunogenicity) of a fixed biological tissue is largely dependant upon the chemical make-up of the tissue (i.e., presence of surface antigens), the type of chemical fixative agent used in fixing the tissue, and the particular methods and conditions used during the fixation (i.e., chemical crosslinking of the connective tissue proteins). Biocompatability-related problems which have known to follow the implantation of a chemically fixed biological grafts and/or prostheses may include: local tissue inflammation, platelet aggregation, host rejection and/or enzymatic degradation of the graft or prosthesis. Like calcification, lack of biocompatability may also result in undesirable post-implantation complications or sequelae.

One method which has been proposed for mitigating the potential for thrombogenesis due to non-biocompatability of a biological graft or prosthesis, is the binding of heparin to the collagen and/or elastin of the implanted biological tissue such that the anti-coagulant properties of the heparin will prevent or deter subsequent thrombogenesis. Heparin is a polysaccharide which consists of alternate residues of L-iduronic acid 2-sulfate and 2-deoxy-2-sulfoaminoglucose 6-sulfate. The anticoagulant properties of heparin are probably due to binding of the heparin molecule to thrombin and antithrombin in plasma in a manner which promotes their subsequent combination. Heparin may also affect lipid metabolism by causing lipoprotein lipase to become bound to cell surfaces.

Heparin may be covalently or ionically bound to collagen or elastin. In the ionic approach, heparin is first ionically bound to protamine to form a heparin-protamine complex. The heparin-protamine complex is then introduced into the collagen or elastin matrix. As a result, heparin is slowly released from the graft into the blood stream. Such slow release of heparin from a lumenal graft (e.g., a tubular vascular graft) may facilitate endothelialization of the lumen of the graft.

Patents and patent applications which have described methods for binding or applying heparin to bioprosthetic materials include: U.S. Pat. No. 4,690,973 Production Process of an Antithrombogenic and Antiadhesive Material for Medical Use (Noishiki Y., Kodaira K., Furuse M., Miyata T., Miyamoto T., and Ito H.) issued Sep. 1, 1987; U.S. Pat. No. 4,704,131 Medical Materials (Noishiki Y., and Miyata T.) issued Nov. 3, 1987; U.S. Pat. No. 4,806,595 Method of Preparing Antithrombogenic Medical Materials (Noishiki Y., Kodaira, K., Furuse, M., and Miyata T.) issued Feb. 21, 1989. Also, the following publications have described methods for binding or applying heparin to bioprosthetic materials: Noishiki Y., Nagaoka S., Kikuchi T., and Mori Y., "Application of Porous Heparinized Polymer to vascular Graft", Trans ASAIO 27:213–218, 1981; Miyata T., Noishiki Y., Matsumae M., and Yamane Y., "A New Method to Give An Antithrombogenicity to Biological materials and Its Successful Application to Vascular Grafts", Trans ASAIO 29:363–368, 1983; Noishiki Y., and Miyata T., "Antiadhesive Collagen Membrane with Heparin Slow Release", The 11th Annual Meeting of the Society for Biomaterials, pp. 99, San Diego, Apr. 25–28, 1985; Noishiki Y., and Miyata T., "Successful Animal Study of Small Caliber Heparin-Protamine-Collagen Vascular Grafts", Trans ASAIO 31:102–106, 1985; Noishiki Y., and Miyata T., "A Simple Method to Heparinize Biological Materials" J Biomed Mater Res 20:337–346, 1986; Noishiki Y., and Miyata T., "Anti-adhesive Collagen Membrane with Heparin Slow Release", J Bioactive Biocompatible Polymers 2:325–333, 1987; Satoh S., Niu S., Shirakata S., Oka T., and Noishiki Y., "Development of an Autologous Connective Tissue Tube as a Small Caliber Vascular Substitute", Trans ASAIO 34:655–660, 1988; Miyata T., Furuse M., and Noishiki Y., "Biodegradable Antiadhesive Collagen Membrane with Heparin Slow Release" The 3rd World Biomaterials Congress, PP. 528, Apr. 21–25, Tokyo, 1988.

One problem which can arise when attempting to covalently bind heparin to chemically fixed biological tissues is that the fixation process may use up the majority of the available amino ($NH_2$) groups on the connective tissue protein molecules (e.g., collagen and elastin), thereby leaving an insufficient number of functional amino groups for subsequent binding to the heparin. Additionally, the few functional amino ($NH_2$) groups which may remain on the connective tissue proteins may be located or situated so as to be less than optimal for subsequent heparin binding.

In view of the above-explained shortcomings of the prior art, there remains a need for the development of new methodologies which will a) enhance the number and/or availability of functional amino groups on the connective tissue proteins, b) optimize the locations of the available amino groups to facilitate their subsequent bonding to heparin, and c) cause heparin to become bound to the chemically fixed connective tissue proteins in a manner which will result in less calcification and/or enhanced biocompatability and/or decreased thrombogenicity of the implanted graft.

SUMMARY OF THE INVENTION

The present invention provides a method for treating a bioprosthetic material to improve its biocompatability, and to minimize post-implantation calcification, platelet activation and thrombogenesis upon or within the implanted graft.

In accordance with the invention, there is provided a method for actively heparinizing a biological material (e.g., cardiac valve, blood vessel, skin, duramatter, pericardium, ligament, tendon, etc.) which contains connective tissue protein(s) (i.e., collagen and/or elastin), said method generally comprising the steps of:

a) treating the biological material with a chemical crosslinking agent to form crosslinkages between and/ or within the connective tissue protein molecules present in the biological material;

b) contacting the biological material with a polyamine compound which has some carboxyl (COOH) functionality (e.g., amino acid peptide or protein);

c) contacting the biological material with a carboxyl activating compound to convert at least some of the free carboxyl (COOH) groups present on i) the connective tissue protein molecules and/or ii) the polyamine (e.g., amino acid, peptide or protein) molecules, into chemical groups which will react with amines (e.g., conversion of the carboxyl (COOH) groups to o-acylisourea groups); and, d) contacting the biological material with heparin such that the heparin will bind to the amino (NH$_2$) groups present on the polyamine compound which has been directly bonded to or mechanically linked with the connective tissue proteins.

The polyamine compound added in step b can be removed prior to beginning step c, or alternatively the compound added in step b may be coincubated with carboxyl activating compound of step c and the biological material to be heparinized. In instances where free carboxyl (COOH) groups are initially present on the connective tissue protein molecules, the activation of those carboxyl (COOH) groups will result in the formation of peptide bonds between some of the amino (NH$_2$) groups of the polyamine compound and those activated carboxyl (o-acylisourea) groups formed on the connective tissue protein molecules. Alternatively, in instances where the connective tissue protein molecules are lacking or deficient in free carboxyl (COOH) groups, but the polyamine compound used in step b does contain some carboxyl groups, the carboxyl activating compound added in step c serve to activate some or all of the carboxyl (COOH) groups present on the polyamine compound (e.g., amino acids, peptides, proteins), thereby allowing the amino groups of the polyamine compound to subsequently react with those activated carboxyl (e.g., o-acylisourea) groups of the polyamine compound to form a polyamine network which is interlocked about the connective tissue protein molecules, thus resulting in substantial bonding of the polyamine molecules to the connective tissue frame work. Due to the ability of the polyamine compound which has functional carboxyl (COOH) groups to react and crosslink to form extended molecules, more amino groups (NH$_2$) will become available for subsequent heparin binding; and, The order of steps b and c may, in some applications, be interchangeable. Also, in many applications, steps b and c may be carried out concurrently by contacting the material with an admixture of the carboxyl-activating agent and the polyamine.

The carboxyl-activating compound used in step c may be any compound which will convert carboxyl (COOH) groups into amine-reactive intermediates, such as active carboxyl moieties (e.g., o-acylisourea groups or other groups having the active CO$^{31}$ moiety) or other chemical groups capable of reacting with amines. The preferred class of carboxyl activating compounds useable for this purpose are the carbodiimides (e.g., 1-ethyl-3-(3-dimethylaminopropyl)-carbodiimide hydrochloride (EDC); dihexylcarbodiimide (DCC); 1-ethyl-3-(4-azonia-4,4-dimethylpentyl) carbodiimide iodide (EAC). In at least some applications of the method, 1-ethyl-3-(3-dimethylaminopropyl)-carbodiimide hydrochloride (EDC) is the presently preferred carboxyl-activating agent. Other types of carboxyl-activating compounds which may be useable for this purpose include: isoxazolium derivatives (e.g., N-ethyl-5-phenylisoxazolium-3'-sulfonate (syn. "Woodward's Reagent K"); chloroformates (e.g., ethylchloroformate or pnitrophenylchloroformate); carbonyldiimadazole (e.g., 1,1'-carbon-yldiimidazole); n-carbalkoxydihy-droquinolines (e.g., n-(ethoxycarbonyl)- 2-ethoxy-1,2-dihydroquinoline (EEOD) and n-(isobutoxycarbonyl)-2-isobutoxy-1,2-dihydroquinoline (IIDQ).

The polyamine used in step b may have a sufficiently high amine functionality that some but not all of the amino groups will become bound to the amine-reactive intermediate formed in step c of the method, thereby allowing unbound functional amine. In this manner, the peptide-bound polyamine side chains and/or mechanically interlocked polyamine network created in steps b and c of the method will provide an increase in the number of functional amino groups present on (or in attachment to) the connective tissue protein molecules. Such increase in the number of functional amino groups (NH$_2$) will allow fixatives which react with and deplete the available amino (NH$_2$) groups on the connective tissue proteins to be utilized for the initial fixation of the material, and the method of the present invention may then be utilized to enhance the number of available amino (NH$_2$) groups located on or connected to the connective tissue proteins, prior to binding of the heparin. Examples of polyamine compounds useable in this method include compounds which have both carboxyl (COOH) and amine (NH$_2$) functionality, such as various amino acids including lysine, ornithine, oligopeptides or polypeptides having multiple carboxyl (COOH) and amino (NH$_2$) groups.

In accordance with one embodiment of the invention, steps b and c of the above-recited method may be carried out concurrently by immersing the previously crosslinked (e.g., fixed) material in an admixture which contains a) a carboxyl-activating compound (e.g., 1-ethyl-3-(3-dimethylaminopropyl)-carbodiimide hydrochloride (EDC) and b) a carboxyl-containing polyamine compound (e.g., lysine). Such mixture may comprise a 50%/50% (v/v) mixture of 4% 1-ethyl-3-(3-dimethylaminopropyl)-carbodiimide hydrochloride (EDC) and 4% lysine, buffered to a pH which is suitable to promote the desired activation of the carboxyl (COOH) groups by EDC and the subsequent reaction of such activated carboxyl groups (e.g., o-acylisourea) with the lysine. A typical pH which is suitable for this purpose is pH=5.

Still further in accordance with the invention, in applications wherein the connective tissue proteins have carboxyl (COOH) groups present thereon, steps b and c of the above-recited method may be carried out concurrently or separately. When steps b and c are carried out separately, the initial exposure of the carboxyl groups on the connective tissue proteins to the carboxyl activating compound in step b will result in activation of those endogenous carboxyl groups, such that the activated carboxyl groups may then react with some of the amino groups present on the polyamine compound introduced in step c. In other applications wherein the connective tissue proteins are devoid or substantially devoid of any carboxyl groups, it may be desirable to carry out steps b and c concurrently, and for the polyamine compound of step c to have endogenous carboxyl groups along with amine functionality. In this regard, the carboxyl activating compound will serve to activate the carboxyl groups present on the polyamine compound, such that the activated carboxyl groups of the polyamine compound may react with some of the amino groups of the polyamine compound thereby causing an interlocking or interlacing of the polyamine molecules about the carboxyl-free connective tissue protein molecules. Thus, even in applications wherein the connective tissue protein molecules are devoid or substantially devoid of carboxyl groups, the method of the present invention may be carried out by causing a mechanical or stearic interlacing or interlocking of the polyamine molecules within the connective tissue protein matrix.

Further objects and advantages of the present invention will become apparent to those skilled in the art upon reading and understanding of the following detailed description of preferred embodiments.

BRIEF DESCRIPTION OF THE DRAWINGS

FIG. 2a is a schematic diagram of collagen molecules which have been crosslinked by a polyepoxy crosslinking agent and which contain free carboxyl side groups.

FIG. 2b is a schematic diagram of the collagen molecules of FIG. 2a following treatment with lysine and EDC in accordance with the present invention.

FIG. 2c is a schematic diagram of the collagen molecules of FIG. 2b following heparinization in accordance with the present invention.

FIG. 3a is a schematic diagram of collagen molecules which have been crosslinked with a polyepoxy crosslinking agent and which are devoid of free carboxyl (COOH) side groups.

FIG. 3b is a schematic diagram of the collagen molecules of FIG. 3a following treatment with lysine and EDC in accordance with the present invention.

FIG. 3c is a schematic diagram of the collagen molecules of FIG. 3b following heparinization in accordance with the present invention.

DECSRIPTION OF THE PREFERRED EMBODIMENTS

The following detailed description and the examples to which it refers are provided for the purpose of describing and illustrating certain embodiments of the invention only, and are not intended to limit the scope of the invention in any way.

i. The Preferred Method

Figure 1:
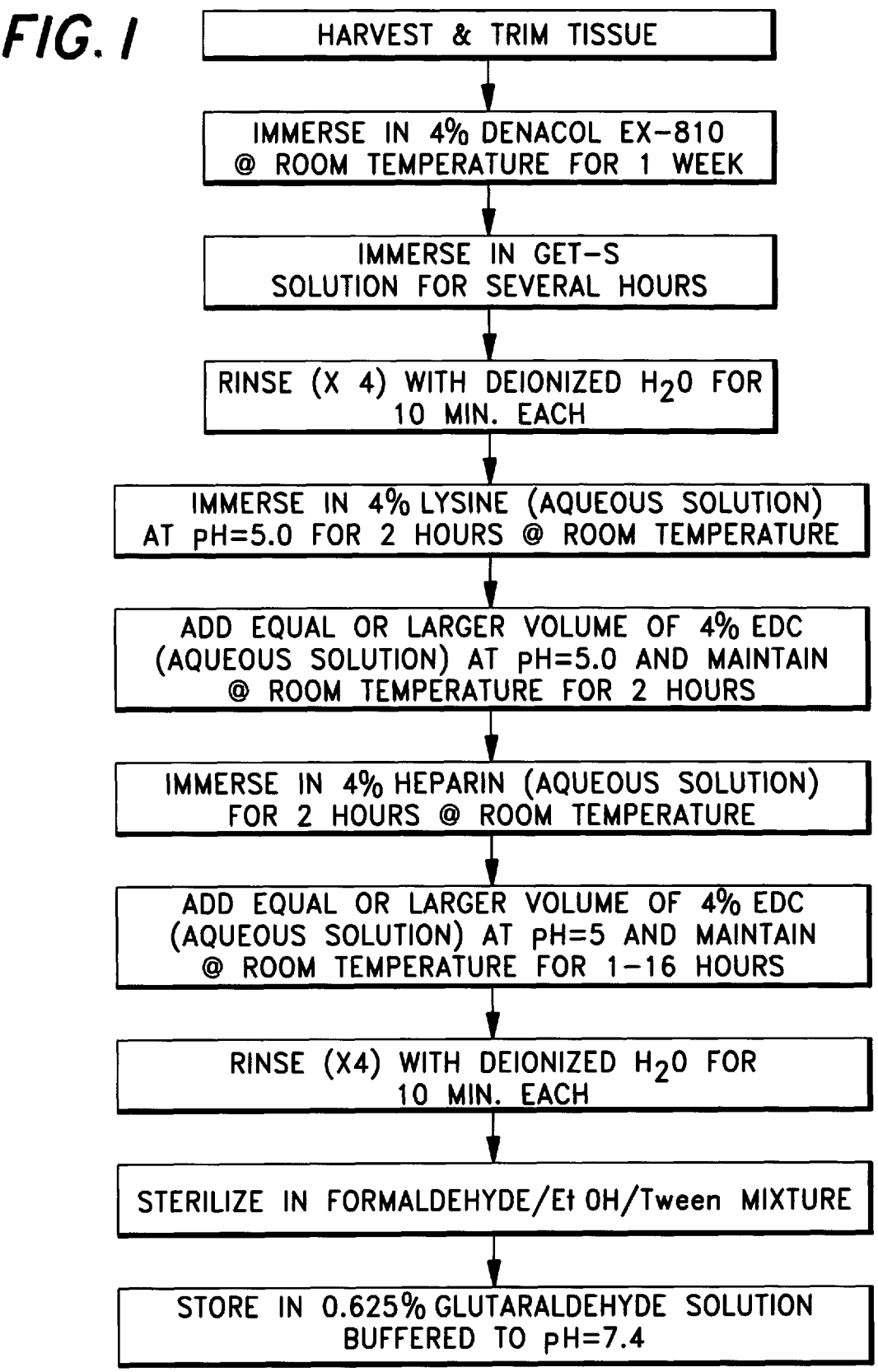
FIG. 1 is a flow diagram of a process for covalently binding heparin to a previously fixed bioprosthetic material.

FIG. 1 shows a flow diagram of a preferred method for treating a biological tissue, such as a segment of bovine pericardium, in accordance with the method of the present invention.

With reference to FIG. 1, an exemplary process for treating a biological tissue (e.g., a segment of bovine pericardium) in accordance with the present invention is as follows:

Step 1: Harvesting and Trimming the Biological Tissue

A suitable collagenous biological tissue, such as segment of bovine pericardium, is harvested from a mammal, trimmed, cleaned and prepared in accordance with standard technique.

Step 2: Crosslinking

In this preferred method, the harvested and trimmed segment of tissue is immersed within a solution of four percent ethylene diglycidyl ether (Denacol EX-810, Nagase Chemical Company, Osaka, Japan) at room temperature, for a period of 1 week. This results in crosslinking of amino ($NH_2$) groups present on the connective tissue proteins (e.g., collagen and elastin molecules) within the tissue. This Denacol fixation may also react with some of the carboxyl (COOH) groups present on the connective tissue protein molecules. It is to be appreciated, however, that many other fixative agents may be used in this step including any chemical agent which will bring about the desired crosslinking of collagen and/or elastin molecules within the tissue. (e.g., glutaraldehyde, dialdehyde starch, etc.) Depending on the type of fixative agent used and the time/conditions of exposure, the connective tissue protein (e.g., collagen and elastin) molecules may or may not have a substantial number of free carboxyl (COOH) groups present thereon. As described more fully herebelow, the remaining steps 3–11 of the method may be carried out irrespective of whether the connective tissue protein molecules include any free carboxyl (COOH) groups.

Step 3: Equilibration/Neutralization/Bioburden Reduction

After the desired crosslinking of the biological tissue has been complete, the tissue is immersed in a neutralization/equilibration/bioburden reduction solution such as a GET-S solution which is made up of glutaraldehyde, ethanol and Tween 80™ surfactant, buffered to a neutral pH with either phosphate or HEPES buffer. Alternatively, one may use a FET-S solution made up of formaldehyde, ethanol and Tween 80™ surfactant buffered to a neutral pH with either phosphate buffer or HEPES buffer.

Step 4: Rinsing

After the neutralization/equilibration/bioburden reduction has been completed, the tissue is removed from the GET-S solution and repeatedly rinsed with a flow of sterile deionized water. In most instances, four (4) consecutive ten (10) minute rinses of this type will be sufficient to remove any residualfixative and/orequilibration/neutralization/bioburdenreductionsolution.

Step 5: Immersion in Lysine Solution

After the tissue has been adequately rinsed, the tissue is immersed in a four percent (4%) aqueous solution of lysine at pH 5 for a period of two (2) hours at room temperature.

Step 6: Addition of Carboxyl Activating Compound

After the tissue has been immersed in the four percent (4%) lysine solution for two (2) hours, a four percent (4%) aqueous solution of EDC (pH 5.0) is added, in equal volume, to the volume of the lysine solution present. This forms an admixture which contains 2% lysine and 2% EDC. Thereafter, the tissue is permitted to remain immersed in this lysine/EDC admixture, at room temperature, for two hours.

Step 7: Heparinization

After the tissue has remained in the lysine-EDC admixture for the above-stated two (2) hour period, the tissue is removed from the lysine-EDC admixture, and is then immersed in a four percent (4%) aqueous solution of heparin for an additional two (2) hours, at room temperature. This results in contact between the heparin and the amino ($NH_2$) groups present on the lysine side chains which have become bound to the activated carboxyl (COOH) groups during the preceding steps (i.e., Steps 5 & 6) of the method.

Step 8: Addition of Carboxyl Activating Solution

After the tissue has remained in the four percent (4%) heparin solution for two hours at room temperature in accordance with Step 7 hereabove, a four percent (4%) aqueous solution of EDC is added in equal volume to the amount of four percent (4%) heparin solution present. This forms an admixture containing essentially 2% heparin and 2% EDC. The pH of this resultant heparin/EDC admixture is adjusted to 5.0 and the tissue is allowed to remain immersed within such heparin/EDC admixture for an additional one (1) to sixteen (16) hours, at room temperature. This allows the activation of carboxyl groups (COOH) in heparin and cross linking between those activated carboxyl groups and the amino ($NH_2$) groups present on the lysine side chains.

Step 9: Rinse

The tissue is then repeatedly rinsed with a flow of sterile deionized water. In most instances, (4) consecutive rinses of ten (10) minutes each will be sufficient to remove any residual heparin and EDC.

Step 10: Sterilization

After the tissue has been adequately rinsed to remove any residual heparin and/or EDC solution, the tissue may be immersed in a liquid sterilant mixture, such as a mixture of 1–10% formaldehyde in ethanol and Tween 80 surfactant. The tissue will be permitted to remain in such liquid sterilant mixture for a period of time suitable to adequately sterilize the tissue. In cases where a mixture of 1–10% formaldehyde in ethanol and Tween 80 is utilized, an immersion time of 5–40 hours will typically be sufficient to effect the desired sterilization.

Step 11: Storage

After the tissue has been sterilized, the tissue may be placed in a suitable storage solution such as 0.625% glutaraldehyde solution buffered to a pH of 7.4. The tissue will remain immersed in such storage solution until time of use.

FIGS. 2a–2c and 3a–3c schematically show the manner in which the preferred method of the invention (e.g., set forth in the flow diagram of FIG. 1) results in the addition of functional amino ($NH_2$) groups to the connective tissue matrix, and the subsequent binding of heparin.

Figure 2A:
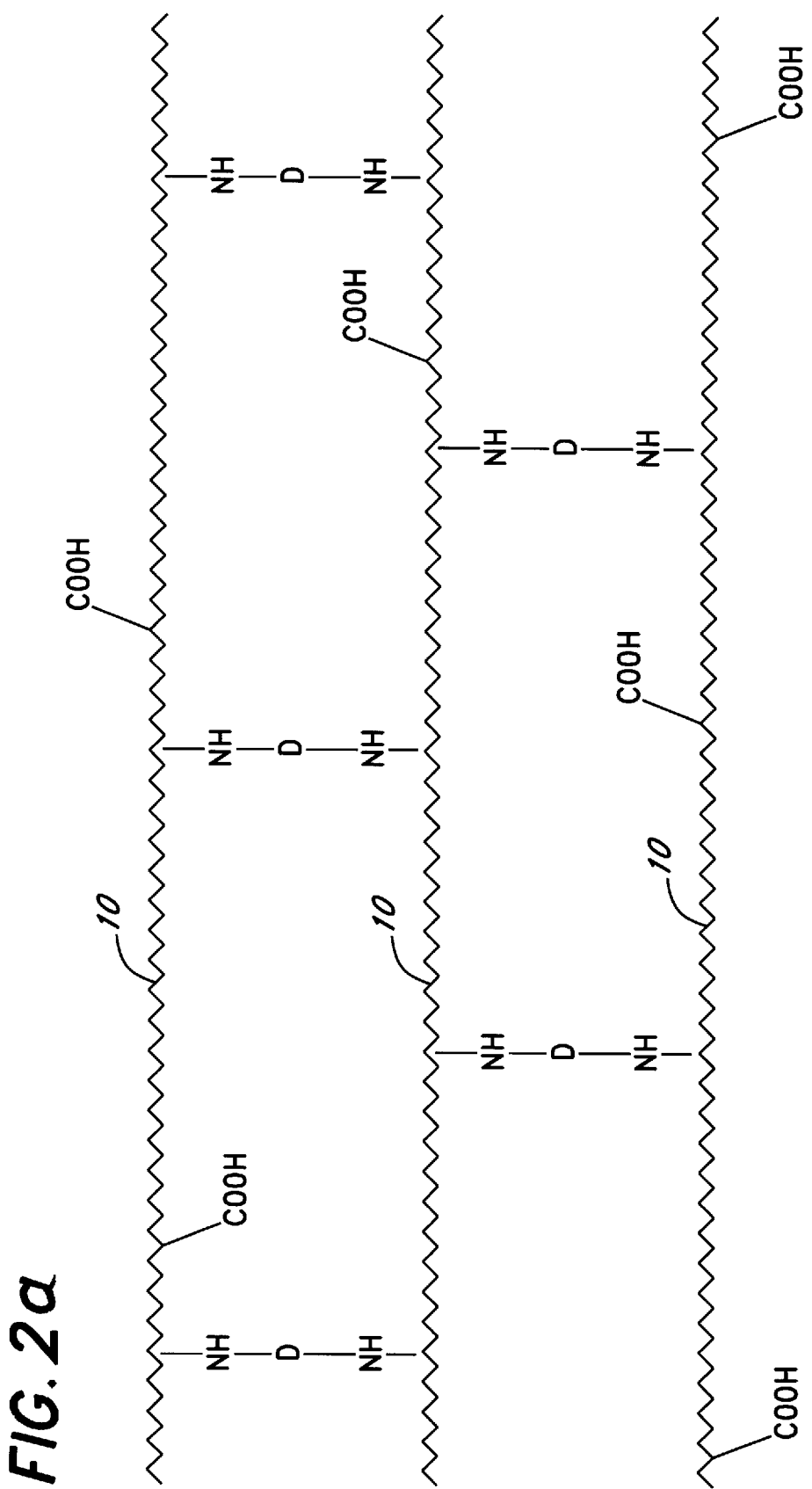
FIGS. 2a–2c provide a step-by-step showing of a method for binding of heparin to a fixed bioprosthetic tissue wherein free carboxyl (COOH) groups are present on the connective tissue protein molecules, as follows.
Figure 2B:
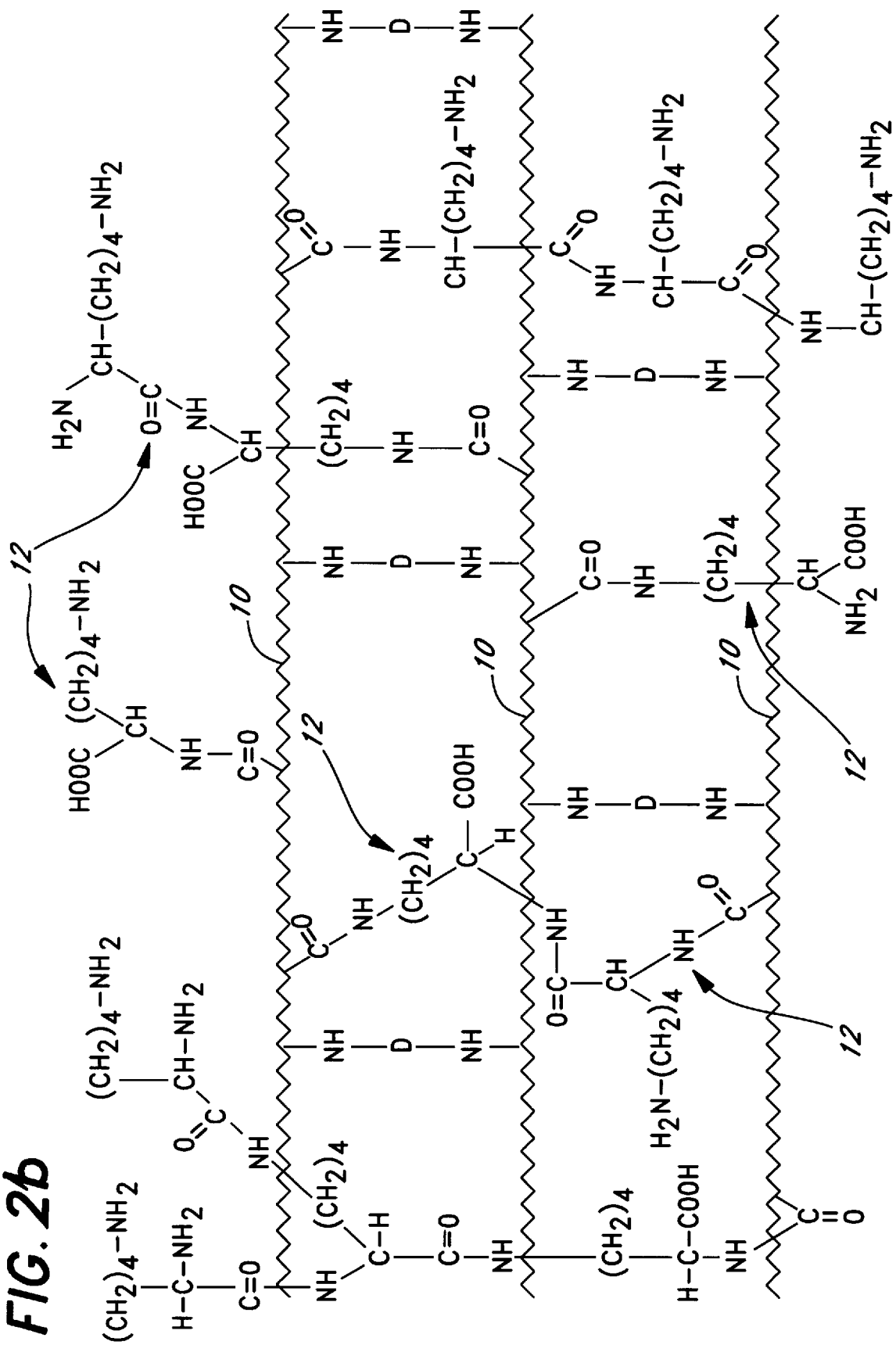
Figure 2C:
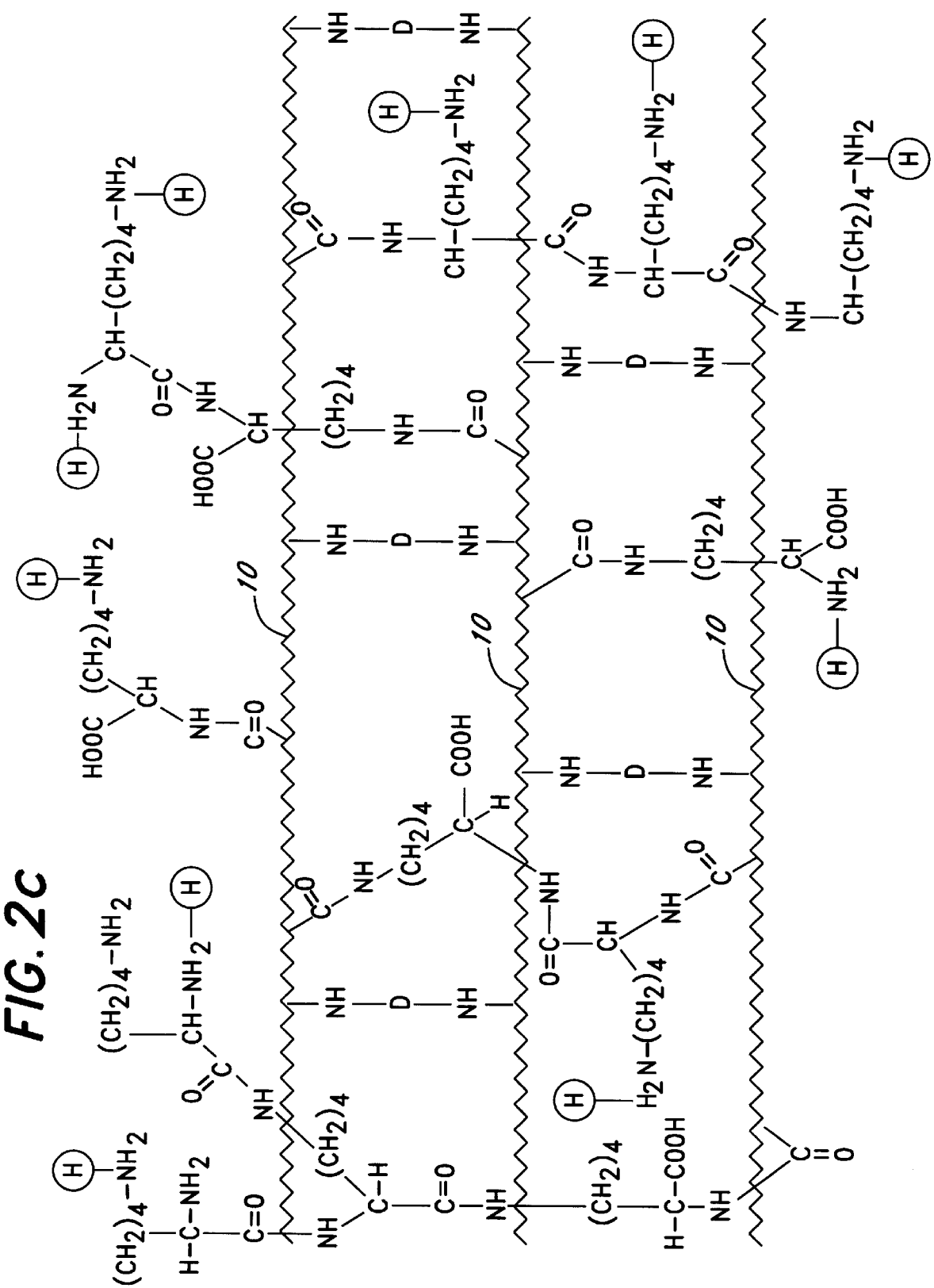
Figure 3A:
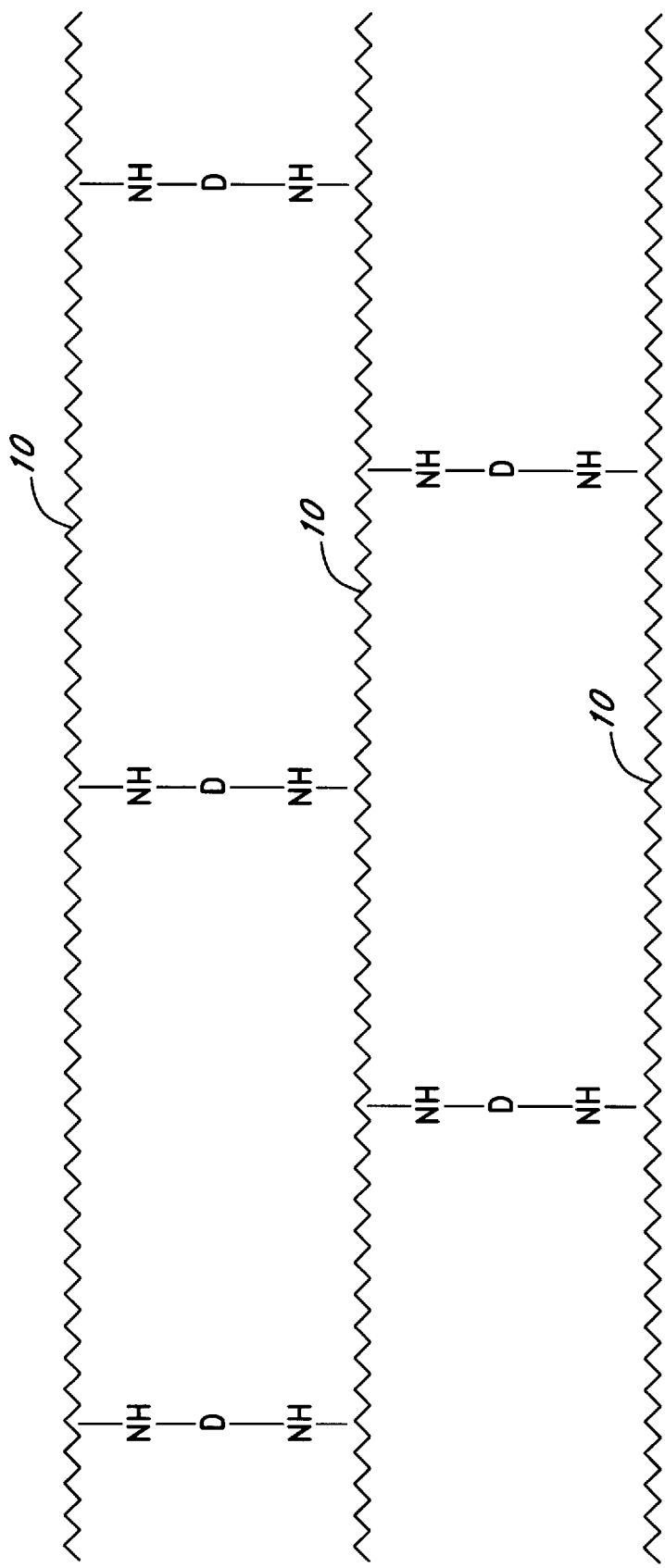
FIGS. 3a–3c provide a step-by-step showing of a method for causing mechanical linkage of heparin to a fixed bioprosthetic tissue wherein the connective tissue protein molecules are devoid of or deficient in free carboxyl (COOH) groups, but wherein the polyamine compound does have free carboxyl (COOH) groups thereon, as follows.
Figure 3B:
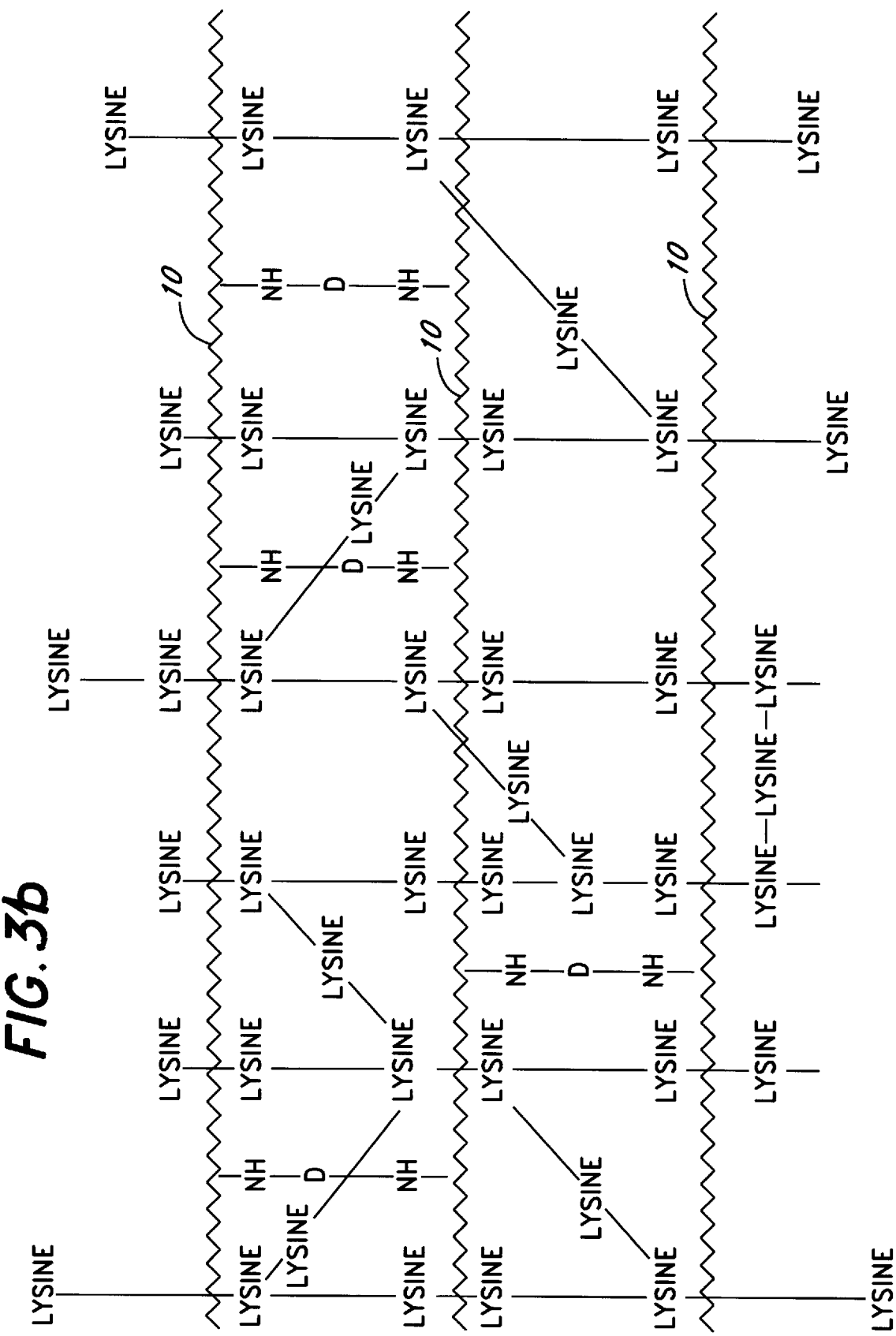
Figure 3C:
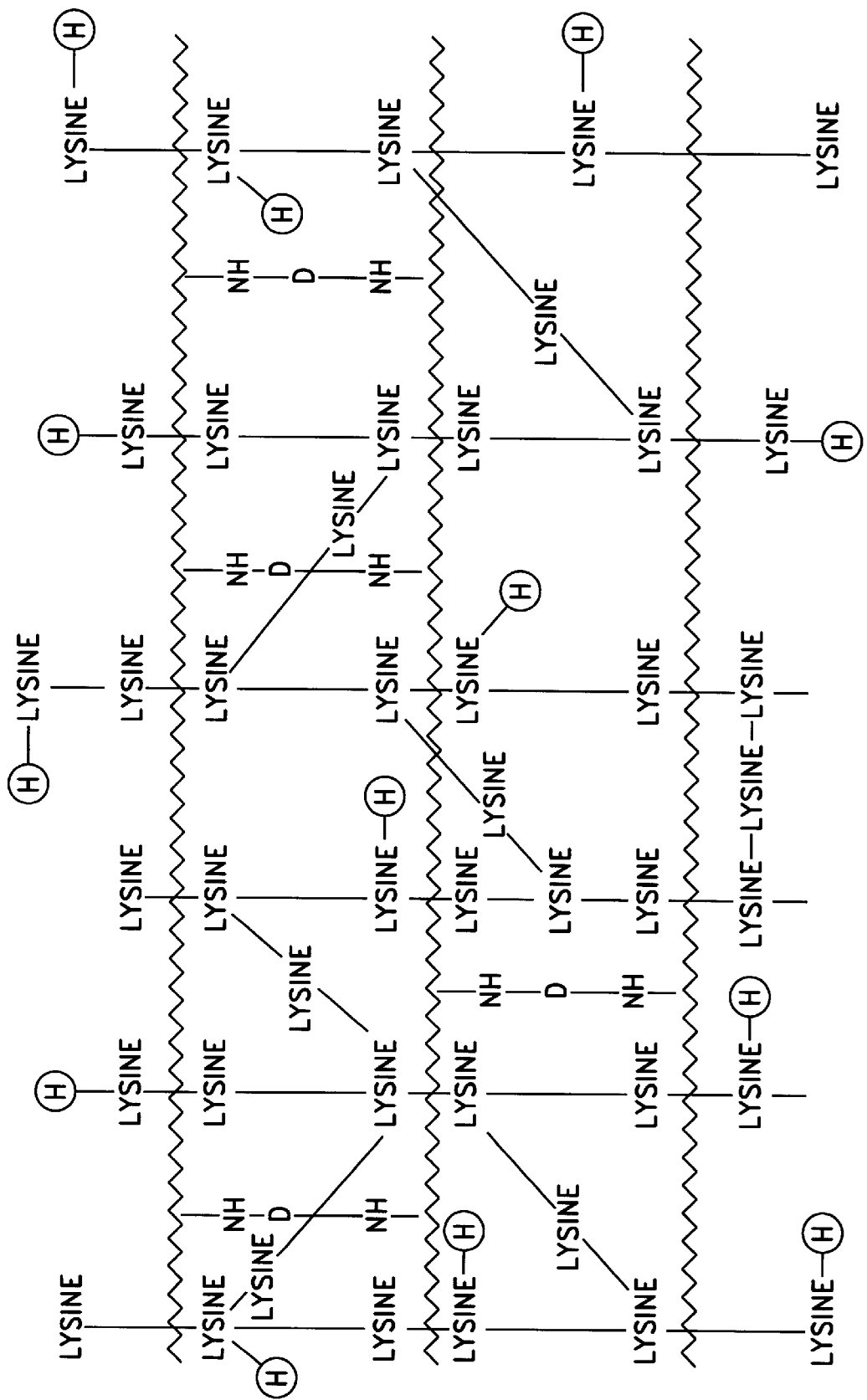

Specifically, FIGS. 3a–3c are directed to an application of the method wherein the connective tissue protein molecules are devoid of or deficient in available carboxyl (COOH) groups. On the other hand, FIGS. 2a–2c are directed to an application wherein a substantial number of available carboxyl (COOH) groups are present on the connective tissue protein molecules of the crosslinked graft material.

ii. Applications of the Preferred Method to Materials Wherein Sufficient Carboxyl (COOH) Groups are Present On The Connective Tissue Protein Molecules With specific reference to FIGS. 2a–2c, there are provided schematic diagrams of collagen molecules 10 having amine ($NH_2$) and carboxyl (COOH) side groups present thereon. A polyepoxy fixative (e.g., Denacol EX 313) has been used to form intermolecular crosslinkages between amino groups of adjacent collagen molecules 10, such crosslinkages being designated by the letter "D". (FIG. 2c) After the polyepoxy crosslinking has been completed, the fixed biological material is treated with lysine and EDC in accordance with steps 5–6 of the preferred method described hereabove. This results in conversion of the carboxyl (COOH) groups of the collagen molecules 10 to o-acylisourea groups, which subsequently react with free amines on the lysine molecules to form peptide-bound lysine side chains 12, as shown in FIG. 2b. These peptide bound lysine side chains have numerous functional amino ($NH_2$) groups which are available for subsequent reaction with heparin.

As shown in FIG. 2c, the heparin provided in step 7 of the preferred method described hereabove becomes covalently bound to amino ($NH_2$) groups on the peptide-bound lysine side chains, thereby resulting in heparinization of the biological material.

iii. Applications of the Preferred Method to Materials Wherein The Connective Tissue Protein Molecules are Devoid of or Deficient in Functional Carboxyl (COOH) Groups With specific reference to the example shown in FIGS. 3a–3c, the method of the present invention may also be employed to promote heparinization of biological materials wherein the connective tissue protein molecules are devoid of free carboxyl (COOH) groups, or are deficient in such carboxyl (COOH) groups (e.g., lack a sufficient number of functional carboxyl (COOH) groups to provide the peptide binding of lysine to the connective tissue protein molecules as in the above-described example of FIG. 2a–2c). In this regard, FIG. 3a shows collagen molecules 10 which have amino ($NH_2$) side groups, but which are devoid of any free carboxyl (COOH) side groups due to other chemical treatments which have depleted such carboxyl (COOH) groups. Intermolecular crosslinkages have been formed by a polyepoxy fixative such as Denacol EX 313, and denoted by "D" on FIG. 3a.

As shown in FIG. 3b, the subsequent exposure of the biological material to lysine and EDC (as in steps 5 & 6 of the preferred method described hereabove) will convert the carboxyl (COOH) groups present on the lysine molecules to amine reactive intermediates (e.g., o-acylisourea groups). Such amine-reactive intermediate will then react with some of the amino groups on the lysine molecules to form peptide-bound lysine network which is mechanically interlocked within the crosslinked collagen matrix of the material.

Thereafter, exposure of the biological material to heparin (as in Step 7 of the preferred method described hereabove) results in covalent binding of heparin H to the remaining free amino groups ($NH_2$) on the mechanically interlocked lysine network, thereby resulting in heparinization of the biological material.

It is to be appreciated that the showings of FIGS. 2a, 2b, 2c, 3a, 3b & 3c are schematic in nature, and do not purport to depict the actual three dimensional molecular structure which will result from application of the methods of the present invention. For example, some of the lysine side chains shown in FIGS. 3b and 3c would, in reality, be partially hidden from view due to their positioning behind the collagen fibers or other structure shown in those Drawings.

iv. Applications of the Method to Other Biological and Non-Biological Materials

Although the methods of the present invention may have considerable utility in relation to bioprosthetic materials having connective tissue protein matrices, it is to be understood that these methods may also be applied to other biological and non-biological materials. For example, natural or synthetic polymer materials having crosslinked or crosslinkable polymer chains in a fluid-permeable network may be subject to heparinization by the methods of the present invention. In instances wherein the polymer chains have carboxyl (COOH) groups present thereon, the method of the present invention may be utilized to form peptide-bound polyamine side chains to which heparin may subsequently be ionically bound, in accordance with the detailed description set forth in section i hereabove. In other instances wherein the polymer molecules are devoid or substantially devoid of carboxyl (COOH) groups, the methods of the present invention may be utilized to form a mechanically interlocked polyamine network within the polymer molecules such that heparin may be subsequently ionically bound to that mechanically interlocked polyamine network in accordance with the detailed description set forth in section ii hereabove.

Examples of natural or synthetic, fluid-permeable polymeric materials which may be heparinized by the methods of the present invention include expanded polytetrafluoroethylene (PTFE) grafts, polyester or other knitted or woven grafts, and biogel matrix made of polyethylene oxide (PEO).

Although the invention has been described with reference to certain presently preferred embodiments, it will be appreciated that various modifications or changes may be made to the above-described embodiments without departing from the intended spirit and scope of the invention. For example, various different fixatives, carboxyl activating compounds, polyamine compounds and other reagents may be utilized to bring about the same molecular reactions and modifications as those described hereabove and shown in the flow diagram of FIG. 1. Accordingly, it is intended that all such reasonable modifications to the above-described preferred embodiment be included within the scope of the following claims.

What is claimed is:

1. A method for heparinizinig a crosslinked biological material which comprises connective tissue protein molecules having amino and carboxyl groups present thereon, said method comprising the steps of:
   a) contacting the biological material with a crosslinking agent which will form crosslinkages between corrective tissue protein molecules;
   b) contacting the biological material with a carboxyl activating compound to convert carboxyl groups present on the connective tissue protein molecules into amine reactive intermediates;
   c) contacting the biological material with a polyamine compound which contains carboxyl group(s), such that amino groups present on the polyamine compound will react with the amine-reactive intermediates formed on the connective tissue proteins, to form covalently-bound amine side chains having functional amino groups thereon; and
   d) contacting the biological material with heparin such that the carboxyl groups on heparin can be activated a then covalently bind to at least some of the functional amino groups present on the covalently-bound amine side chains.

2. The method of claim 1 wherein step a comprises contacting the biological material with a crosslinking agent selected from the group of crosslinking agents consisting of:
   a) glutaraldehyde;
   b) a dialdehyde compound;
   c) a polyepoxy compound;
   d) a bisimidoester;
   e) bis-N-succinimidyl; and,
   f) a diisocyanate.

3. The method of claim 1 wherein step b comprises contacting the biological material with a carboxyl activating compound selected from the group of carboxyl activating compounds consisting of:
   carbodiimides;
   1-ethyl-3-(3-dimethylaminopropyl)-carbodiimide hydrochloride (EDC);
   dihexylcarbodiimide (DCC); and,
   1-ethyl-3-(4-azonia-4,4-dimethylpentyl)carbodiimide iodide (EAC).

4. The method of claim 3 wherein step a comprises contacting the biological material with a crosslinking agent selected from the group of crosslinking agents consisting of:
   a) glutaraldehyde;
   b) a dialdehyde compound;
   c) a polyepoxy compound;
   d) a bisimidoester;
   e) bis-N-succinimidyl; and,
   f) a diisocyanate.

5. The method of claim 4 wherein the method further comprises the step of:
   e) placing the material in a sterilant solution for a period of time sufficient to cause sterilization of the tissue.

6. The method of claim 5 wherein the method further comprises the step of:
   f) after removing the material from the sterilant solution, storing the material in a glutaraldehyde-containing solution.

7. The method of claim 3 wherein the polyamine compound utilized in step c of the method is selected from the group of polyamine compounds consisting of:
   a) lysine;
   b) hydroxylysine;
   c) ornithine;
   d) an oligopeptide containing multiple amino groups and carboxyl groups; and,
   e) a polypeptide containing multiple amino groups and carboxyl groups.

8. The method of claim 3 wherein steps b and c are carried out concurrently by contacting the biological tissue with a mixture which contains a carboxyl activating compound and a polyamine compound to result in the formation of covalent bonds between the tissue and the polyamine compound.

9. The method of claim 1 wherein the polyamine compound utilized in step c of the method is selected from the group of polyamine compounds consisting of:
   lysine;
   hydroxylysine;
   ornithine;
   an oligopeptide containing multiple amino groups and carboxyl groups; and,
   a polypeptide containing multiple amino groups and carboxyl groups.

10. The method of claim 1 wherein steps b and c are carried out concurrently by contacting the biological tissue with a mixture which contains the carboxyl activating compound and the polyamine compound to form covalent bonds between the tissue and the polyamine compound.

11. A method for heparinizing a crosslinked biological material which comprises connective tissue protein molecules having amino and carboxyl groups present thereon, said method comprising the steps of:
   a) contacting the biological material with ethylene diglycidyl ether to form covalent crosslinkages between amino groups of the connective tissue proteins;
   b) contacting the biological material with a lysine solution for 0.5–20 hours;
   c) adding to the lysine solution of step b, an EDC solution to provide a lysine/EDC admixture, and thereafter maintaining the biological material in contact with the lysine/EDC admixture for more than approximately 1 hour IQ form covalent bonds between the lysine and the tissue;
   d) removing the biological material from lysine/EDC admixture;
   e) contacting the biological material with a heparin solution for 0.5–20 hours;
   f) adding to the heparin solution of step e an EDC solution to provide an EDC/heparin admixture, and maintaining the biological material in contact with the EDC/heparin admixture for 0.5–20 hours to form covalent bonds between the heparin and the covalently-bonded lysine.

12. The method of claim 11 wherein the method further comprises the step of:
   g) placing the biological material in a sterilant solution for a period of time sufficient to cause sterilization of the tissue.

13. The method of claim 12 wherein the method further comprises the step of:

h) after removing the biological material from the sterilant solution, storing the biological material in a glutaraldehyde-containing solution.

14. The method of claim 11 wherein, between steps a and b, there is performed the additional step of:

contacting the biological tissue with a bioburden reduction solution comprising glutaraldehyde, ethanol and a surfactant said solution having a pH of 6.5 to 8.0.

15. The method of claim 14 wherein, after the biological material has been placed in contact with the bioburden reduction solution, but before beginning step b, there is performed the additional step of:

rinsing the biological material with water.

16. The method of claim 15 wherein the additional step of rinsing the biological material with water comprises:

rinsing the biological material four times with deionized water, each rinse lasting for approximately 10 minutes.

17. The method of claim 11 wherein the ethylene diglycidyl ether used in step a is a 4% aqueous solution of ethylene diglycidyl ether.

18. The method of claim 11 wherein the lysine solution used in step b is a 4% aqueous lysine solution.

19. The method of claim 18 wherein the 4% aqueous lysine solution has a pH of approximately 5.0.

20. A method for heparinizing a biological material which comprises connective tissue protein molecules having amino groups present thereon, said method comprising the steps of:

a) contacting the biological material with a crosslinking agent to form covalent crosslinkages between the connective tissue protein molecules;

b) contacting the biological material with i) a polyamine compound having carboxyl groups present thereon and a ii) carboxyl-activating compound to convert at least some of the carboxyl groups present on the polyamine molecules to amine-reactive intermediates, such that at least some of the amino groups present on the polyamine molecules will covalently react with at least some of the amine-reactive intermediates formed on the polyamine molecules, thereby forming a covalently-bound polyamine network which is interlocked with the connective tissue protein molecules; and c) contacting the biological material with heparin and carboxyl group-activating compound such that the heparin will coyalently bind to at least some of the amino groups present on the polyamine network.

21. The method of claim 20 wherein step a comprises contacting the biological material with a crosslinking agent selected from the group of crosslinking agents consisting of:

a) glutaraldehyde;
b) a dialdehyde compound;
c) a polyepoxy compound;
d) a bisimidoester;
e) bis-N-succinimidyl; and,
f) a diisocyanate.

22. The method of claim 20 wherein the polyamine compound utilized in step b of the method is selected from the group of polyamine compounds consisting of:

lysine;
hydroxylysine;
ornithine;
an oligopeptide containing multiple amino groups and carboxyl group(s); and,
a polypeptide containing multiple amino groups and carboxyl groups.

23. A method for heparinizing a crosslinked biological material which comprises connective tissue protein molecules having amino groups present thereon, said method comprising the steps of:

a) contacting the biological material with ethylene diglycidyl ether to form covalent crosslinkages between amino groups of the connective tissue proteins;

b) contacting the biological material with a lysine solution for 0.5–20 hours;

c) adding to the lysine solution of step b, an EDC solution to provide a lysine/EDC admixture, and thereafter maintaining the biological material in contact with the lysine/EDC admixture for 0.5–20 hours to form covalent bonds between the lysine and the tissue;

d) removing the biological material from lysine/EDC admixture;

e) contacting the biological material with a heparin solution for 0.5–20 hours;

f) adding to the heparin solution of step e an EDC solution to provide an EDC/heparin admixture, and maintaining the biological material in contact with the EDC/heparin admixture for 0.5–20 hours to form covalent bonds between the heparin and the covalently-bonded lysine.

24. The method of claim 23 wherein the method further comprises the step of:

g) placing the biological material in a sterilant solution for a period of time sufficient to cause sterilization of the tissue.

25. The method of claim 24 wherein the method further comprises the step of:

h) after removing the biological material from the sterilant solution, storing the biological material in a glutaraldehyde-containing solution.

26. The method of claim 23 wherein, between steps a and b, there is performed the additional step of:

contacting the biological tissue with a bioburden reduction solution comprising glutaraldehyde, ethanol and a surfactant said solution having a pH 6.5 to 8.0.

27. The method of claim 26 wherein, after the biological material has been placed in contact with the bioburden reduction solution, but before beginning step b, there is performed the additional step of:

rinsing the biological material with water.

28. The method of claim 27 wherein the additional step of rinsing the biological material with water comprises:

rinsing the biological material four times with deionized water, each rinse lasting for approximately 10 minutes.

29. The method of claim 23 wherein the ethylene diglycidyl ether used in step a is a 4% aqueous solution of ethylene diglycidyl ether.

30. The method of claim 23 wherein the lysine solution used in step b is a 4% aqueous lysine solution.

31. The method of claim 30 wherein the 4% aqueous lysine solution has a pH of approximately 5.0.

32. A method of heparinizing a permeable polymeric material which comprises polymer molecules having intermolecular crosslinkages formed therebetween, said method comprising the steps of:

a) contacting the material with a polyamine compound having carboxyl groups present thereon, and a carboxyl-activating compound to convert at least some of the carboxyl groups present on the polyamine molecules to amine-reactive intermediates, such that at least some of the amino groups present on the polyamine molecules will C!covalently react with at least some of the amine-reactive intermediates formed on the polyamine molecules, thereby forming a polyamine network which is interlocked within [a] the polymer molecules; and, thereafter, b) contacting the material with heparin and a carboxyl-activating compound such that the heparin will covalently bind to at least some of the amino groups present on the polyamine network;

c) placing the material with the covalently-bound heparin in a sterilant solution for a period of time sufficient to cause sterilization of the tissue; and d) after removing the material from the sterilant solution, storing the material in a glutaraldehyde-containing solution.

33. The method of claim 32 comprising the additional step of:

contacting the material with a bioburden reduction solution comprising glutaraldehyde, ethanol and a surfactant at a pH of 6.5 to 8.0.

34. A method of heparinizing a permeable polymeric material which comprises polymer molecules having intermolecular crosslinkages formed therebetween, said method comprising the steps of:

a) contacting the material with a polyamine compound having carboxyl groups present thereon, and a carboxyl-activating compound to convert at least some of the carboxyl groups present on the polyamine molecules to amine-reactive intermediates, such that at least some of the amino groups present on the polyamine molecules will covalently react with at least some of the amine-reactive intermediates formed on the polyamine molecules, thereby forming a polyamine network which is interlocked within the polymer molecules; and, thereafter, b) contacting the material with heparin and a carboxyl-activating compound such that the heparin will covalently bind to at least some of the amino groups present on the polyamine network;

c) contacting the material with a bioburden reduction solution comprising glutaraldehyde, ethanol and a surfactant at a pH of 6.5 to 8.0.

* * * * *